United States Patent
Huang et al.

(10) Patent No.: US 12,383,186 B2
(45) Date of Patent: Aug. 12, 2025

(54) ELECTROENCEPHALOGRAM MEASUREMENT STRUCTURE

(71) Applicant: NATIONAL APPLIED RESEARCH LABORATORIES, Taipei (TW)

(72) Inventors: Chun-Ming Huang, Hsinchu (TW); Chen-Chia Chen, Hsinchu (TW); Gang-Neng Sung, Hsinchu (TW); Chien-Ming Wu, Tainan (TW)

(73) Assignee: National Applied Research Laboratories, Taipei (TW)

( * ) Notice: Subject to any disclaimer, the term of this patent is extended or adjusted under 35 U.S.C. 154(b) by 824 days.

(21) Appl. No.: 17/337,666

(22) Filed: Jun. 3, 2021

(65) Prior Publication Data
US 2022/0304614 A1  Sep. 29, 2022

(30) Foreign Application Priority Data
Mar. 23, 2021  (TW) .................. 110110393

(51) Int. Cl.
| *A61B 5/369* | (2021.01) |
| *A61B 5/00* | (2006.01) |
| *A61B 5/273* | (2021.01) |
| *H04R 1/10* | (2006.01) |

(52) U.S. Cl.
CPC .............. *A61B 5/369* (2021.01); *A61B 5/273* (2021.01); *A61B 5/6815* (2013.01); *H04R 1/1025* (2013.01); *A61B 2562/166* (2013.01)

(58) Field of Classification Search
None
See application file for complete search history.

(56) References Cited

U.S. PATENT DOCUMENTS

| 3,815,583 A | * | 6/1974 | Scheidt ................ A61B 5/0002 600/479 |
| 2017/0041699 A1 | * | 2/2017 | Mackellar .......... A61B 5/02405 |
| 2017/0071495 A1 | | 3/2017 | Denison et al. |

FOREIGN PATENT DOCUMENTS

| CN | 2812458 Y | 8/2006 |
| CN | 208640704 U | 3/2019 |
| CN | 210042148 U | 2/2020 |
| TW | I331027 B | 10/2010 |

OTHER PUBLICATIONS

Kappel, Simon, et al., "Ear-EEG Forward Models: Improved Head-Models for Ear-EEG," Sep. 10, 2019, Frontiers in Neuroscience, vol. 13, Article 943, pp. 1-13 (Year: 2019).*

* cited by examiner

*Primary Examiner* — Aurelie H Tu
(74) *Attorney, Agent, or Firm* — Rosenberg, Klein & Lee

(57) ABSTRACT

The present invention provides an electroencephalogram measurement structure formed by an ear-hanging structure and a second circuit board. The ear-hanging structure includes a body. An ear-hanging member is disposed at the extension of the body. The body can be worn on the ear via the ear-hanging member. In addition, a first reference electrode and a second reference electrode are disposed on the body and coupled to a first circuit board. The first circuit board is coupled to an electrical jack; the second circuit board is coupled to the electrical jack via an electrical plug. Thereby, the electroencephalogram measurement can be performed simply by wearing the ear-hanging member on the ear of the person under test. Hence, the problems of complicated wiring and inconvenience in wearing can be solved concurrently.

4 Claims, 2 Drawing Sheets

ELECTROENCEPHALOGRAM MEASUREMENT STRUCTURE

FIELD OF THE INVENTION

The present invention relates to an electroencephalogram measurement structure.

BACKGROUND OF THE INVENTION

As the awareness of health increases in modern times, people's demand in understanding their health condition increases gradually. In addition, the significant development in medical technologies drives the global market in mobile health equipment to grow annually, leading to raised demand in mobile measurement of electrophysiological signals such as the electrocardiography (ECG), the electromyography (EMG), the electrooculography (EOG), and the electroencephalography (EEG). The supplier in the field are devoted aggressively in the design and development of related technologies.

The measurement of electrophysiological signals according to the prior art requires attachment of numerous electrodes and wires on the body part under test of a person. Then the electrophysiological signals are transmitted back to a single monitor. The measurement locations and numbers for different electrophysiological signals differ, the monitor for electrophysiological signals must be customized. In addition, since the measurement of electrophysiological signals requires a common reference voltage, the electrodes and the monitor for electrophysiological signals cannot adopt wireless designs. Furthermore, the person under test cannot move freely during the measurement process.

To measure the EEG, for example, electrodes should be attached to the scalp of the person under test with wires connected. An instrument receives the signals and amplifies the voltages representing the neural activities of the brain. According to the prior art, an exclusive cap with internal multiple electrode for contacting the scalp is adopted. The electrodes are connected to wires. The various signals received the wires will be collected to a signal box for further processing and displaying the electroencephalogram.

In general, a plurality of electrodes and a plurality of wires are required for a measurement device for electro- physiological signals of electroencephalogram. According to the measurement items, the electrodes are attached on corresponding location of the scalp. The electrodes are classified into dry electrodes and wet electrodes. The former uses probes to pass through the hair and touch the scalp, while the latter require conductive glue thereon for smooth electrical conduction. Nonetheless, both methods require usage of the plurality of electrodes and wires, making the wearing complicated. Besides, the person under test needs to bear the weight of the electrodes and wires.

According to the above description, the present invention provides an electroencephalogram measurement structure, which is worn on the ear of a person under test via an ear-hanging member of an ear-hanging structure. A first reference electrode and a second reference electrode on the body of the ear-hanging structure are coupled to a first circuit board. The first circuit board is coupled to an electrical jack; the second circuit board is coupled to an electrical plug. The electrical plug is coupled to the electrical jack. In addition, the second circuit board is also coupled to a measurement electrode for measuring electroencephalogram. The wearing method is quite simple and convenient, and hence solving the problems of complicated wiring and inconvenience in wearing according to the prior art.

SUMMARY

An objective of the present invention is to provide an electroencephalogram measurement structure formed by an ear-hanging structure and a second circuit board. The ear-hanging structure includes a body. An ear-hanging member is disposed at the extension of the body. The body can be worn on the ear via the ear-hanging member. In addition, a first reference electrode and a second reference electrode are disposed on the body and coupled to a first circuit board. The first circuit board is coupled to an electrical jack; the second circuit board is coupled to the electrical jack via an electrical plug. Thereby, the electroencephalogram measurement can be performed simply by wearing the ear-hanging member on the ear of the person under test. Hence, the problems of complicated wiring and inconvenience in wearing can be solved concurrently.

To achieve the above objective, the present invention provides an electroencephalogram measurement structure, which comprises an ear-hanging structure and a second circuit board. The ear-hanging structure includes a body. An ear-hanging member is disposed on the extension of one end of the body. A reference first electrode and a second reference electrode are disposed adjacent to each other on one side of the body. The first reference electrode and the second reference electrode are coupled to a first circuit board. The first circuit board is coupled to an electrical jack. The first circuit board is disposed inside the body. The second circuit board is coupled to an electrical plug and a measurement electrode, respectively. The electrical plug is coupled to the electrical jack.

According to an embodiment of the present invention, the ear-hanging structure includes the ear-hanging member, a flexible member, and a hollow housing. One end of the flexible member is lodged in the ear-hanging member. The other end of the flexible member is lodged in the hollow housing.

According to an embodiment of the present invention, the first reference electrode and the second reference electrode correspond to and contact a reference part of a human body for detecting a reference electrophysiological signal of the reference part.

According to an embodiment of the present invention, the measurement electrode corresponds to a sensing part of a human body for sensing an electrophysiological signal of the sensing part.

DETAILED DESCRIPTION

In order to make the structure and characteristics as well as the effectiveness of the present invention to be further understood and recognized, the detailed description of the present invention is provided as follows along with embodiments and accompanying figures.

The electrodes for measuring electroencephalogram according to the prior art are classified into dry electrodes and wet electrodes. The former uses probes to pass through the hair and touch the scalp, while the latter require conductive glue thereon for smooth electrical conduction. Nonetheless, both methods require usage of the plurality of electrodes and wires, making the wearing complicated. Besides, the person under test needs to bear the weight of the electrodes and wires. The present invention provides an electroencephalogram measurement structure formed by an ear-hanging structure and a second circuit board. The ear-hanging structure includes a body. An ear-hanging member is disposed at the extension of the body. The body can be worn on the ear via the ear-hanging member. In addition, a first reference electrode and a second reference electrode are disposed on the body and coupled to a first circuit board. The first circuit board is coupled to an electrical jack; the second circuit board is coupled to the electrical jack via an electrical plug. Thereby, the electroencephalogram measurement can be performed simply by wearing the ear-hanging member on the ear of the person under test. Hence, the problems of complicated wiring and inconvenience in wearing can be solved concurrently.

In the following description, various embodiments of the present invention are described using figures for describing the present invention in detail. Nonetheless, the concepts of the present invention can be embodied by various forms. Those embodiments are not used to limit the scope and range of the present invention.

Figure 1:
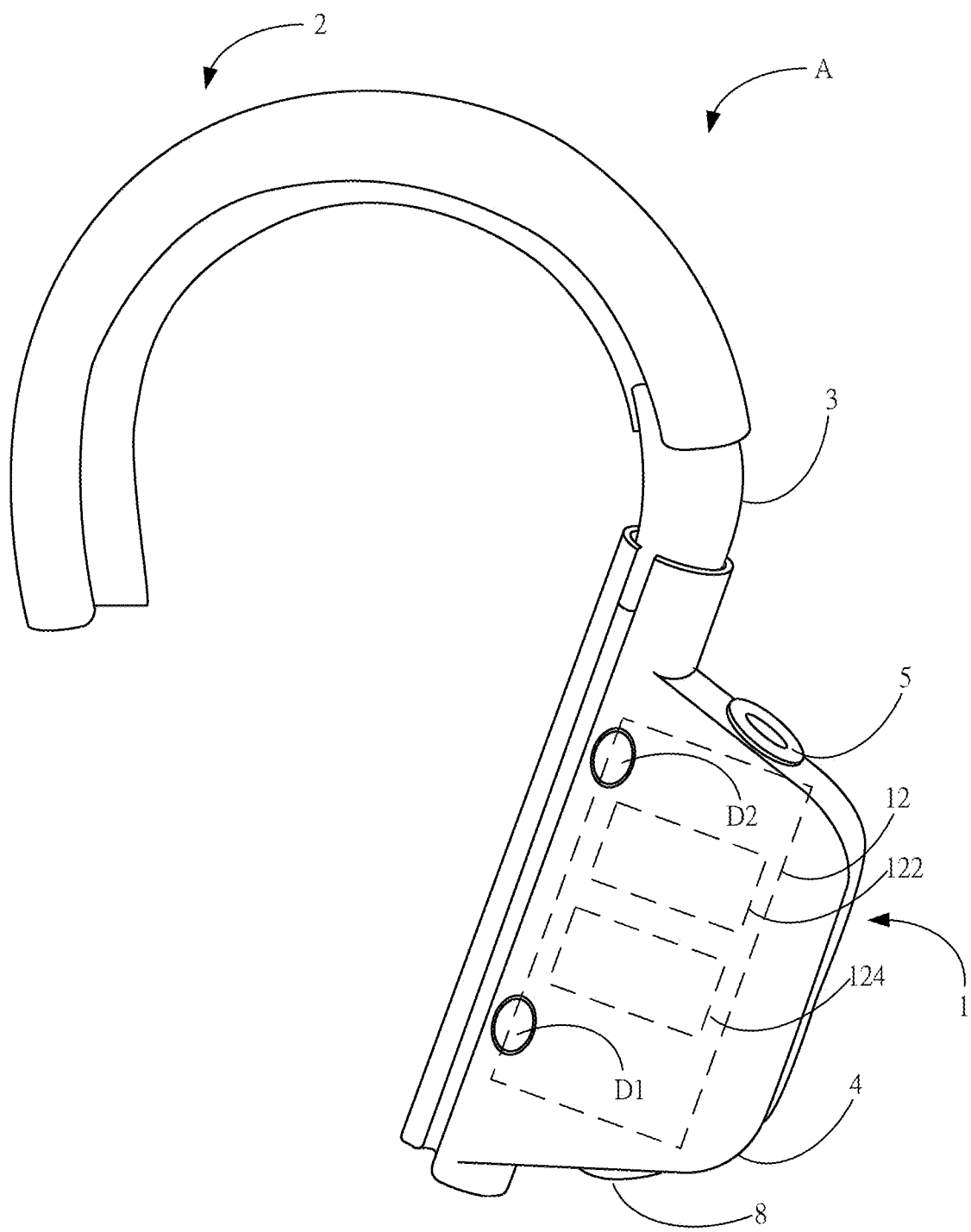
FIG. 1 shows a structural view of the device according to an embodiment of the present invention.

First, please refer to FIG. 1, which shows a structural view of the device according to an embodiment of the present invention. As shown in the figure, the electroencephalogram measurement structure according to the present embodiment comprises an ear-hanging structure A, a body 1, a flexible member 3, a hollow housing 4, an electrical jack 5, an electrical plug 6, a measurement electrode 7, a first reference electrode D1, a second reference electrode D2, and a second circuit board R. The structures will be described as follows.

The electroencephalogram measurement structure according to the present embodiment comprises the ear-hanging structure A, which includes the body 1. An ear-hanging member 2 is disposed on the extension of one end of the body 1. The reference first electrode D1 and the second reference electrode D2 are disposed adjacent to each other on one side of the body 1. In addition, the first reference electrode D1 and the second reference electrode D2 are coupled to a first circuit board 12. The first circuit board 12 is disposed inside the body 1 and coupled to the electrical jack 5.

The ear-hanging structure A according to the present embodiment further includes the ear-hanging member 2, the flexible member 3, and the hollow housing 4. The ear-hanging structure A is formed by connecting the ear-hanging member 2, the flexible member 3, and the hollow housing 4. The ear-hanging member 2 includes a member body 21, and the member body 21 includes a first lodged opening 211. The hollow housing 4 further includes a lodged part 41, and the lodged part 41 includes a second lodged opening 411. The ear-hanging structure A can be bent for adapting to ears with difference sizes by taking advantage of the elasticity of the material of the flexible member 3 while one end of the flexible member 3 is lodged in the first lodged opening 211 of the hollow part 21 and an other end of the flexible member 3 is lodged in the second lodged opening 411 of the lodged part 41. Thereby, the material of the flexible member 3 must be elastic materials, such as rubber, silicone, or soft metals.

According to the present embodiment, the first reference electrode D1 and the second reference electrode D2 correspond to and contact a reference part H1 of a human body H for detecting a reference electrophysiological signal of the reference part H1. The reference part H1 is the part behind the ear on the head. Nonetheless, the location is not limited to the part; it can be adjusted according to the condition. The measurement electrode Z corresponds to a sensing part H2 of a human body H for sensing an electrophysiological signal of the sensing part H2. The sensing part H2 is the location to measure the electrophysiological signal with the reference electrophysiological signal as the baseline.

According to the present embodiment, a charging jack 8 can be further disposed below the body 1. The first circuit board 12 inside the body 1 is coupled to the public supply mains via the charging jack 8.

Figure 2:
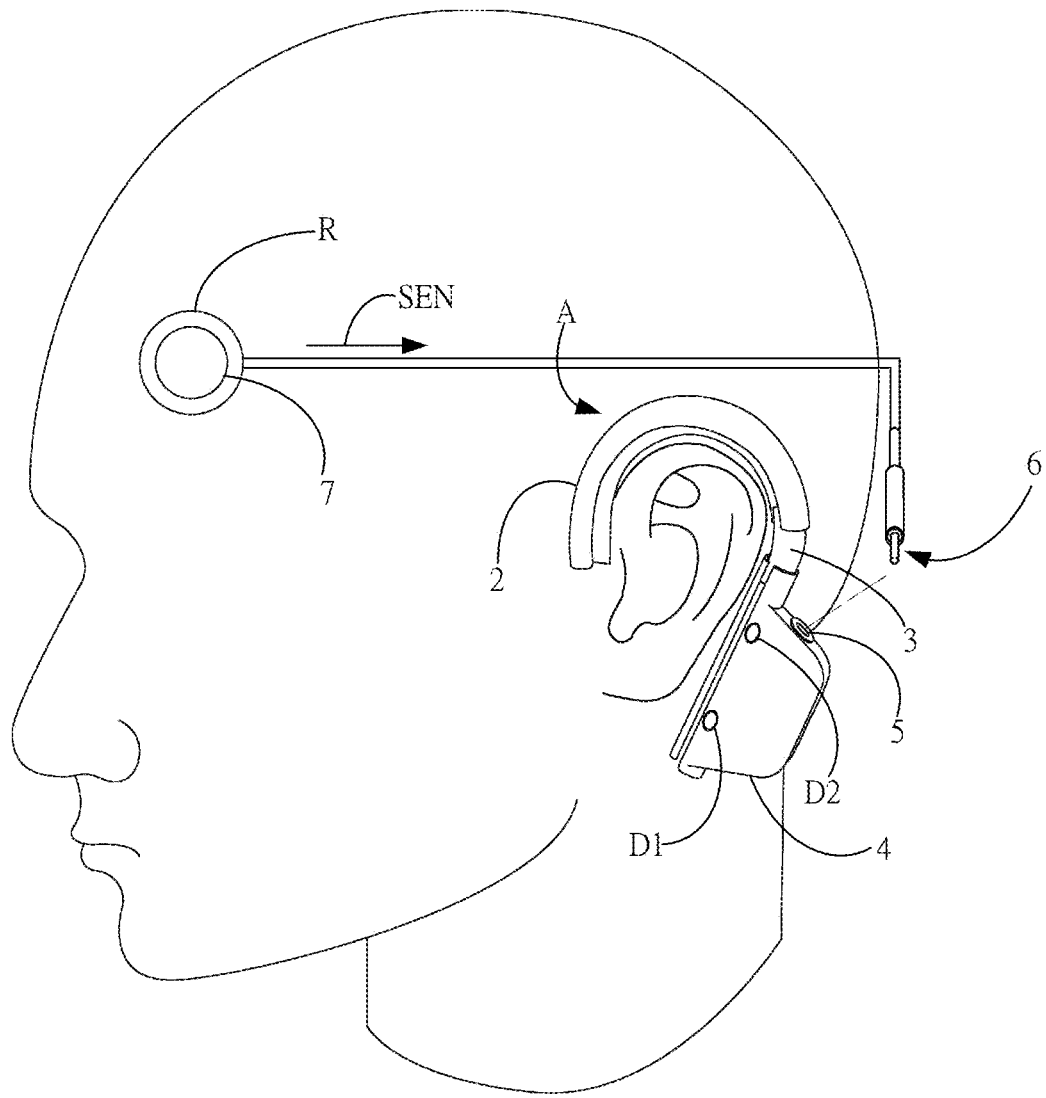
FIG. 2 shows a schematic diagram of wearing the device according to an embodiment of the present invention.

Please refer to FIG. 1 and FIG. 2. FIG. 2 shows a schematic diagram of wearing the device according to an embodiment of the present invention. As shown in the figures, according to the present embodiment, the second circuit board R is coupled electrically to the electrical plug 6 and the measurement electrode 7, respectively. In addition, the electrical plug 6 is coupled to the electrical jack 5. The second circuit board R according to the present embodiment is a transparent flexible circuit board, and is coupled to the electrical plug 6 via the wire L extended from the second circuit board R. The measurement electrode 7 is disposed on the second circuit board R for measuring electroencephalogram. The electrophysiological signal SEN from the measurement electrode 7 is transmitted to the first circuit board 12 via the electrical plug 6 using the wire L. Nonetheless, the present invention is not limited to the embodiment. Different flexible circuit boards can be adopted according to the types of electrophysiological signals to be measured. For example, the number of the measurement electrode 7 can be increased hence the size of the second circuit board R should be changed. Alternatively, the material of the measurement electrode 7 can be changed to a flexible circuit board suitable for measuring electromyogram.

According to the present embodiment, the first circuit board 12 includes a processing unit 122. The first circuit board 12 receives the electrophysiological signal SEN from the measurement electrode 7. The processing unit 122 converts the signal format of the electrophysiological signal SEN from the analog format to a signal format accessible by computers, such as a digital format. The processing unit 122 can further filter the electrophysiological signal SEN for filtering out noises. Besides, the first circuit board 12 further includes a wireless transmission device 124, which can transmit the electrophysiological signal SEN measured by the measurement electrode 7 to an electronic device (not shown in the figures) directly and wirelessly. For example, the electrophysiological signal SEN can be transmitted to a smartphone, a server, or a personal computer using the Wi-Fi, the Bluetooth, or the 4G/5G mobile communication for monitoring. Alternatively, the wireless transmission device 124 can transmit the electrophysiological signal SEN processed by the processing unit 122 to the electronic device wirelessly.

According to the above embodiment, the present invention provides an electroencephalogram measurement structure, which is worn on the ear of a person under test via a hollow ear-hanging member of an ear-hanging structure. A first reference electrode and a second reference electrode on the body of the ear-hanging structure are coupled to a first circuit board. The first circuit board is coupled to an electrical jack; the second circuit board is coupled to an electrical plug. The electrical plug is coupled to the electrical jack. In addition, the second circuit board is also coupled to a measurement electrode for measuring electroencephalogram. The wearing method is quite simple and convenient, and hence solving the problems of complicated wiring and inconvenience in wearing according to the prior art.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. An electroencephalogram measurement structure, comprising:

an ear-hanging structure, including a body, having an ear-hanging member disposed on one end of said body, having a first reference electrode and a second reference electrode, said first reference electrode and said second reference electrode disposed adjacent to each other, said first reference electrode and said second reference electrode disposed on one side of said body, said first reference electrode and said second reference electrode coupled to a first circuit board and configure to detect a reference electrophysiological signal at a reference part of a human body, said first circuit board coupled to an electrical jack, and said first circuit board disposed inside said body, said ear-hanging member configured for hanging on an ear of said human body; and a second circuit board, coupled to an electrical plug and a measurement electrode, respectively, said measurement electrode configured to sense an electrophysiological signal, and said electrical plug coupled to said electrical jack and configured to transmit said electrophysiological signal from said measurement electrode to said first circuit board through said electrical jack.

2. The electroencephalogram measurement structure of claim 1, wherein said ear-hanging structure includes:

a member body, said member body including a first lodged opening;

a flexible member, with one end lodged in said first lodged opening of said member body; and a hollow housing, including a lodged part, said lodged part including a second lodged opening, an other end of said flexible member is lodged into said second lodged opening.

3. The electroencephalogram measurement structure of claim 1, wherein said first reference electrode and said second reference electrode correspond to and are configured to contact a reference part of said human body for detecting a reference electrophysiological signal of said reference part.

4. The electroencephalogram measurement structure of claim 1, wherein said measurement electrode is configured to sense said electrophysiological signal at a sensing part of said human body.

* * * * *